US008545879B2

(12) United States Patent
Burns et al.

(10) Patent No.: US 8,545,879 B2
(45) Date of Patent: Oct. 1, 2013

(54) FAST DISINTEGRATING COMPOSITIONS OF MELOXICAM

(75) Inventors: David Allen Burns, Wilmington, NC (US); Gregory Edward Neal, Swindon (GB)

(73) Assignees: Wilmington Pharmaceuticals, LLC, Wilmington, NC (US); R.P. Scherer Techonologies, Inc., Somerset, NJ (US)

( * ) Notice: Subject to any disclaimer, the term of this patent is extended or adjusted under 35 U.S.C. 154(b) by 0 days.

(21) Appl. No.: 12/988,919

(22) PCT Filed: Aug. 31, 2010

(86) PCT No.: PCT/US2010/047254
§ 371 (c)(1),
(2), (4) Date: May 9, 2011

(87) PCT Pub. No.: WO2011/026080
PCT Pub. Date: Mar. 3, 2011

(65) Prior Publication Data
US 2012/0168335 A1    Jul. 5, 2012

Related U.S. Application Data

(60) Provisional application No. 61/238,265, filed on Aug. 31, 2009.

(51) Int. Cl.
*A61K 9/64* (2006.01)
*A61K 9/20* (2006.01)
*A61K 31/54* (2006.01)

(52) U.S. Cl.
USPC .................... 424/456; 424/464; 514/226.5

(58) Field of Classification Search
USPC ................ 424/456, 464; 514/226.5
See application file for complete search history.

(56) References Cited

U.S. PATENT DOCUMENTS

| | | | |
|---|---|---|---|
| 4,233,299 A * | 11/1980 | Trummlitz et al. | ........ 514/226.5 |
| 4,305,502 A | 12/1981 | Gregory et al. | |
| 4,371,516 A | 2/1983 | Gregory et al. | |
| 5,046,618 A | 9/1991 | Wood | |
| 5,188,825 A | 2/1993 | Iles et al. | |
| 5,343,672 A | 9/1994 | Kearney et al. | |
| 5,358,118 A | 10/1994 | Thompson et al. | |
| 5,457,895 A | 10/1995 | Thompson et al. | |
| 5,558,880 A | 9/1996 | Gole et al. | |
| 5,631,023 A | 5/1997 | Kearney et al. | |
| 5,648,093 A | 7/1997 | Gole et al. | |
| 5,729,958 A | 3/1998 | Kearney et al. | |
| 5,738,875 A | 4/1998 | Yarwood et al. | |
| 5,827,541 A | 10/1998 | Yarwood et al. | |
| 5,837,287 A | 11/1998 | Yarwood et al. | |
| 5,976,577 A | 11/1999 | Green et al. | |
| 6,083,531 A | 7/2000 | Humbert-Droz et al. | |
| 6,156,339 A | 12/2000 | Grother et al. | |
| 6,212,791 B1 | 4/2001 | Thompson et al. | |
| 6,297,240 B1 | 10/2001 | Embleton | |
| 6,316,027 B1 | 11/2001 | Johnson et al. | |
| 6,342,246 B2 | 1/2002 | Johnson et al. | |
| 6,413,549 B2 | 7/2002 | Green et al. | |
| 6,423,342 B1 | 7/2002 | Jordan et al. | |
| 6,509,040 B1 | 1/2003 | Murray et al. | |
| 6,588,180 B2 | 7/2003 | Heath et al. | |
| 6,680,071 B1 | 1/2004 | Johnson et al. | |
| 6,709,669 B1 * | 3/2004 | Murray et al. | ................. 424/434 |
| 6,726,928 B2 | 4/2004 | Yarwood et al. | |
| 6,830,153 B2 | 12/2004 | French et al. | |
| 6,890,472 B2 | 5/2005 | Heath | |
| 7,121,822 B2 | 10/2006 | Heath | |
| 7,325,703 B2 | 2/2008 | Gherdan et al. | |
| 2002/0074257 A1 | 6/2002 | Heath | |
| 2002/0197321 A1 | 12/2002 | Seager | |
| 2004/0023948 A1 | 2/2004 | Green et al. | |
| 2004/0156894 A1 | 8/2004 | Grother et al. | |
| 2004/0265377 A1 | 12/2004 | Seager | |
| 2005/0073068 A1 | 4/2005 | Kearney et al. | |
| 2005/0106241 A1 | 5/2005 | Brewer et al. | |
| 2005/0181182 A1 | 8/2005 | Heath | |
| 2006/0134194 A1 | 6/2006 | Banbury et al. | |
| 2009/0197874 A1 | 8/2009 | Stroppolo et al. | |

FOREIGN PATENT DOCUMENTS

| | | | |
|---|---|---|---|
| DE | 2 756 113 A1 | 6/1979 | |
| EP | 1250921 A1 * | 10/2002 | |
| GB | 1 548 022 A | 7/1979 | |
| GB | 2 111 423 A | 7/1983 | |
| WO | WO2006/041843 | 4/2006 | |

OTHER PUBLICATIONS

International Search Report and Written Opinion for Corresponding PCT application No. PCT/US2010/047254, Date of Mailing Oct. 14, 2010.
International Preliminary Report on Patentability of International Application No. PCT/US2010/047254, issued Mar. 15, 2012 (9 pages).
International Preliminary Report on Patentability Corresponding to International Application No. PCT/US2010/047254; Date of Mailing: Mar. 15, 2012; 9 Pages.

(Continued)

*Primary Examiner* — Kevin E Weddington
(74) *Attorney, Agent, or Firm* — Myers Bigel Sibley & Sajovec, P.A.

(57) ABSTRACT

The invention provides pharmaceutical compositions comprising a therapeutically effective amount of meloxicam, or a pharmaceutically acceptable salt thereof, wherein the pharmaceutical compositions are in the form of a fast disintegrating dosage form suitable for releasing meloxicam rapidly in the oral cavity. Also provided are processes for preparing a pharmaceutical composition of the invention. Further provided are methods of treating arthritis or pain in a subject in need thereof, the method comprising orally administering to the subject a therapeutically effective amount of a pharmaceutical composition according to the invention.

24 Claims, 1 Drawing Sheet

(56) References Cited

OTHER PUBLICATIONS

Lees, P et al., "Pharmacodynamics and pharmacokinetics of miloxicam in the horse", *British Veterinary Journal*, vol. 147, Issue 2, Mar.-Apr. 1991, pp. 97-108.
The Merck Index, 12 Ed. p. 993 (1996).
The Physicians' Desk Reference, 56th Ed. pp. 1054-1057 (2002).
Tsai, R.-S et al., "Physicochemical and Structural Properties of Non-Steroidal Anti-inflammatory Oxicams", *Helvetica Chimica Acta*, vol. 76, Issue 2, 1993, pp. 842-854.
Wojtulewski, JA et al., "A six-month double-blind trial to compare the efficacy and safety of meloxicam 7.5 mg daily and naproxen 750 mg daily in patients with rheumatoid arthritis", *British Journal Rheumatology*, Apr. 1996: 35 Suppl 1:22-28.

* cited by examiner

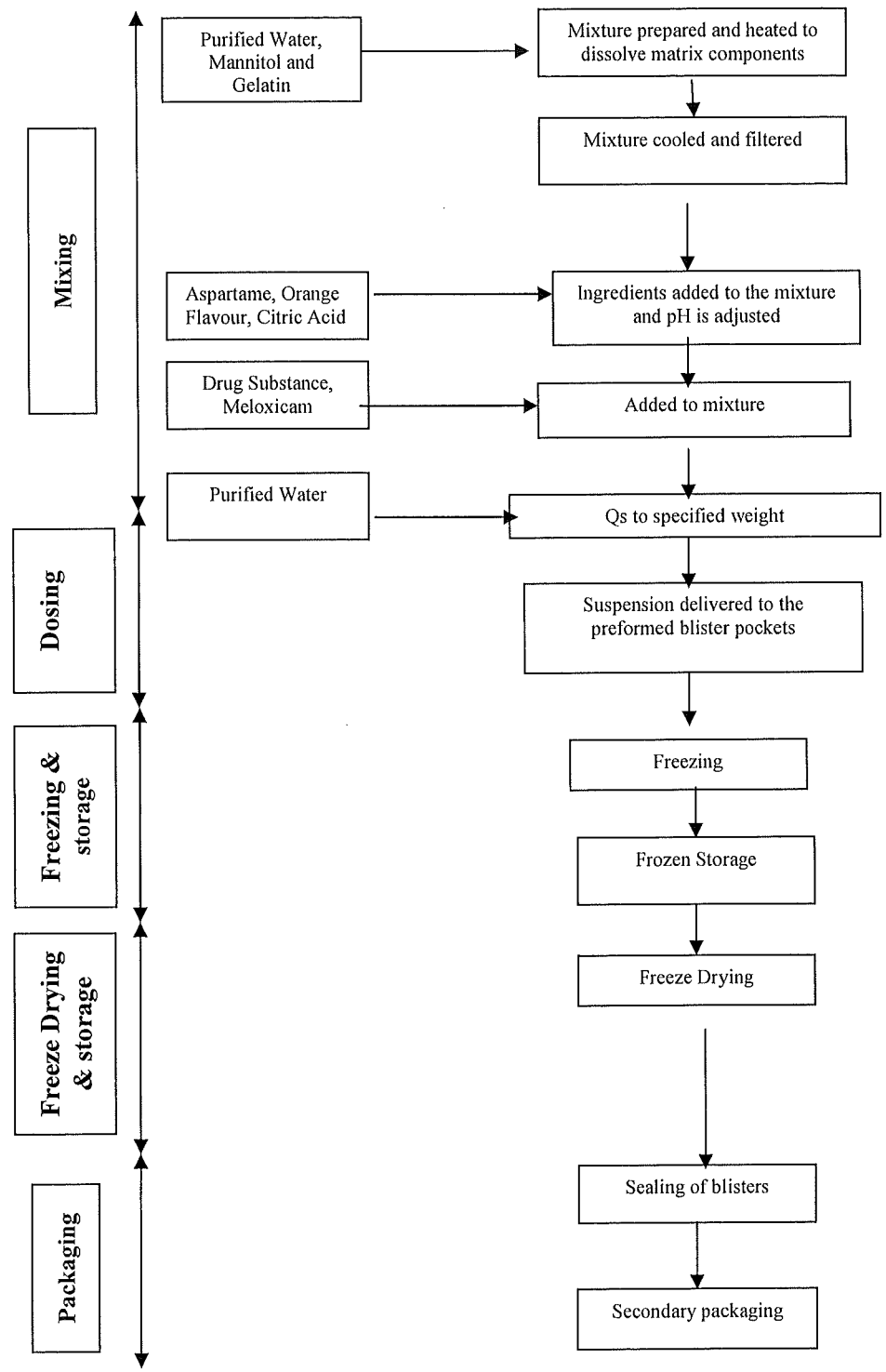

FAST DISINTEGRATING COMPOSITIONS OF MELOXICAM

RELATED APPLICATIONS

This application is a 35 U.S.C. §371 national phase application of PCT Application PCT/US2010/047254, filed Aug. 31, 2010, and which claims the benefit under 35 U.S.C. §119(e) of U.S. Provisional Patent Application Ser. No. 61/238,265, filed Aug. 31, 2009, the disclosures of which are incorporated herein by reference in their entireties.

FIELD OF THE INVENTION

The present invention generally relates to oral compositions of meloxicam, processes for preparation thereof, and methods of using the pharmaceutical compositions of the invention to treat arthritis and/or pain.

BACKGROUND OF THE INVENTION

Meloxicam is a nonsteroidal anti-inflammatory drug (NSAID) of the oxicam class with analgesic and antipyretic properties. Meloxicam inhibits prostaglandin synthetase (cylooxygenase (COX) 1 and 2) and leads to a decrease of the synthesis of prostaglandins, which contribute to inflammation of joints. Many commercially available NSAID drugs are COX inhibitors, which inhibit both COX1 and COX2. A general inhibition of COX may provide the benefits of anti-inflammatory, analgesic and antipyretic effects. However, it also causes serious side effects such as digestive disorders and renal disorders. It is believed that COX1 is constitutively expressed in most organs (e.g., stomach or kidney). See Vane et al., Proc. Natl. Acad. Sci. USA, 91:2046-2050 (1994); Oulette et al., Proc. Natl. Acad. Sci., 98:14583-14588 (2001); and Seibert et al., Proc. Natl. Acad. Sci., 91:12013-12017 (1994). In contrast, COX-2 is induced by various inflammatory mediators or endotoxin in local inflammatory areas. See Smith et al., Proc. Natl. Acad. Sci., 95:13313-13318 (1998). Meloxicam is a selective COX2 inhibitor, which may avoid the side effects of COX1 inhibitors.

Currently, meloxicam is available in both injectable and oral dosage forms (tablet and suspension) for humans. In addition, it has also been approved for veterinary uses for dogs in the U.S. and for cats in Europe, Australia and New Zealand. Some of the trade names under which meloxicam has been or is marketed include MOBIC®, MOBEC®, MOBICOX®, MOVALIS®, and MOVATEC®. The form of meloxicam currently marketed in the United States is MOBIC®, provided in 7.5 and 15 mg tablets.

Meloxicam has been shown to be useful in the symptomatic treatment of painful osteoarthritis (arthrosis, degenerative joint disease), symptomatic treatment of rheumatoid arthritis, and symptomatic treatment of the signs and symptoms of osteoarthritis, including pain, stiffness, and inflammation. Because of meloxicam's broad uses, there is an industrial need to provide an oral dosage form with an improved ease of administration and patient compliance.

SUMMARY OF THE INVENTION

Accordingly, as a first aspect, the invention provides a pharmaceutical composition comprising a therapeutically effective amount of meloxicam, or a pharmaceutically acceptable salt thereof, wherein the pharmaceutical composition is in the form of a fast disintegrating dosage form suitable for releasing meloxicam rapidly in the oral cavity.

A further aspect of the invention provides a process for preparing a pharmaceutical composition of meloxicam comprising the steps of:

(1) preparing a mixture of a therapeutically effective amount of meloxicam, at least one matrix former, and a dispersing agent, (2) filling said mixture into one or more depressions in a tray;

(3) freezing said mixture in said trays so as to form a solid state of the mixtures; and (4) removing the dispersing agent so as to form a solid tablet of the pharmaceutical composition.

In still a further embodiment, the invention provides a method of treating arthritis and/or pain in a subject in need thereof. The method comprises orally administering to the subject a therapeutically effective amount of a pharmaceutical composition described herein.

In one aspect of the invention, the use of a pharmaceutical composition according to the invention for the manufacture of a medicament for the treatment of arthritis and/or pain is provided. Also provided is a pharmaceutical composition described herein for treating arthritis and/or pain.

These and other aspects of the invention are set forth in more detail in the following description of the invention.

BRIEF DESCRIPTION OF THE DRAWINGS

The following drawing forms part of the present specification and is included to further demonstrate certain aspects of the present invention. The invention may be better understood by reference to this drawing in combination with the detailed description of specific embodiments presented herein.

FIG. 1 is an exemplary flow chart of a process for preparing an oral fast disintegrating dosage form of meloxicam.

DETAILED DESCRIPTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

All patents, patent applications and publications referred to herein are incorporated by reference in their entirety. In case of a conflict in terminology, the present specification is controlling.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. Unless otherwise defined, all terms, including technical and scientific terms used in the description, have the same meaning as commonly understood by one of ordinary skill in the art to which this invention belongs.

As used herein, a "therapeutically effective" or "therapeutically acceptable" amount refers to an amount that will elicit a therapeutically useful response in a subject. The therapeutically useful response may provide some alleviation, mitigation, and/or decrease in at least one clinical symptom in the subject. Those skilled in the art will appreciate that the therapeutically useful response need not be complete or curative, as long as some benefit is provided to the subject. In some embodiments, the subject is a mammal. In some embodiments, the subject is a human.

As used herein, the terms "treatment," "treat," and "treating" refer to reversing, alleviating, delaying the onset of, and/or inhibiting the progress of a disease or disorder as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Subjects to be treated by the methods of the present invention include both avian and mammalian subjects. Mammals include, but are not limited to, humans, non-human mammals, non-human primates (e.g. monkeys, chimpanzees, baboons), dogs, cats, mice, hamsters, rats, horses, cows, pigs, rabbits, sheep and goats. Avian subjects include but are not limited to chickens, turkeys, ducks, geese, quail and pheasant, and birds kept as pets (e.g. parakeets, parrots, macaws, cockatoos, and the like.) Subjects may be male or female and may be of any age, including neonatal, infant, juvenile, adolescent, adult, and geriatric subjects.

Active compounds of the present invention may optionally be administered in combination (or in conjunction) with other active compounds and/or agents useful in the treatment of arthritis and/or pain. The administration of two or more compounds "in combination" or "in conjunction" means that the two compounds are administered closely enough in time to have a combined effect, for example an additive and/or synergistic effect. The two compounds may be administered simultaneously (concurrently) or sequentially. Simultaneous administration may be carried out by mixing the compounds prior to administration, or by administering the compounds at the same point in time but at different anatomic sites or using different routes of administration. In some embodiments, the other agent is administered concurrently.

I. Active Compound (Meloxicam)

Meloxicam, also known as 4-hydroxy-2-methyl-N-(5-methyl-2-thiazolyl)-2-H-1,2-benzothiazine-3-carboxamide 1,1-dioxide is an oxicam derivative with the following chemical structure:

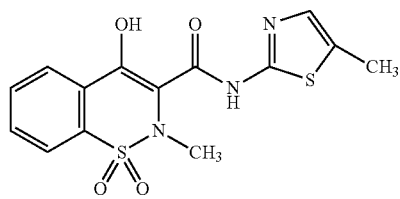 [SMILES: Cc1cnc(NC(=O)C2=C(O)c3ccccc3S(=O)(=O)N2C)s1]

Meloxicam has an empirical formula of $C_{14}H_{13}N_3O_4S_2$ and a molecular weight of 351.41. See The Physicians' Desk Reference, $56^{th}$ Ed, pp. 1054 (2002); and The Merck Index, $13^{th}$ Ed., pp. 1040-1041 (Merck & Co. 2001).

The free form (un-ionized) of meloxicam and salts thereof, as well as methods of preparing these compounds, pharmaceutical compositions including them as active ingredients, and methods of using them as antiphlogistics, are discussed in U.S. Pat. No. 4,233,299. (See also German Patent No. 2,756,113). The pharmacology of meloxicam in horses is discussed in Lees et al., Brit. Vet. J, 147: 97 (1991); veterinary trials in dogs are discussed in Henderson et al., Prakt. Tierarzt., 75:179 (1994); the physiochemical properties of meloxicam are discussed in Tsai et al., Helv. Chim. Acta, 76:842 (1993); the pharmacology, mechanism of action, and clinical efficacy are discussed in Brit. J. Rheumatol., 35(Suppl. 1): 1-77 (1996); and clinical trials of gastrointestinal tolerability in arthritis are discussed in Hawkey et al., Brit. J. Rheumatol., 37:937 (1998), and Dequeker et al., Brit. J Rheumatol., 37:946 (1998).

Any applicable form of meloxicam may be used in the present invention. However, in one embodiment, meloxicam is selected from a crystalline phase, an amorphous phase, a semi-crystalline phase, a semi-amorphous phase, and any combination thereof.

When an appropriate acid or base is used, Meloxicam may be administered as a pharmaceutically acceptable salt. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In some embodiments, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

II. Formulation

Some aspects of the present invention provide compositions comprising, consisting essentially of or consisting of, a therapeutically effective amount of meloxicam or a pharmaceutically acceptable salt thereof, wherein the pharmaceutical composition is in the form of a fast disintegrating dosage form suitable for releasing meloxicam rapidly, for example, in the oral cavity. In the formulations described herein, all weight percentages are with reference to the amount of active ingredient (e.g. meloxicam), or an excipient, or a matrix former relative to the weight of the finished oral dosage form of the pharmaceutical composition (e.g. a dried tablet).

Any applicable fast dissolving dosage form that is known to one skilled in the art may be applied to the pharmaceutical compositions described herein.

The term "fast disintegration dosage form", as used herein, refers to pharmaceutical compositions which disintegrate in no more than about 2 minutes, or 90 seconds or 60 seconds in the oral cavity (e.g., mouth). In some embodiments, the pharmaceutical compositions disintegrate in less than about 30 seconds in the oral cavity. In another embodiment, the pharmaceutical compositions disintegrate in less than about 10 seconds or about 5 seconds in the oral cavity. In another embodiment, the pharmaceutical compositions disintegrate in less than about 3 seconds in the oral cavity.

In one embodiment, the free form of meloxicam may be used in the present invention. In some embodiments, the amount of meloxicam is in the range of about 5 mg to 20 mg. In a further embodiment, the amount of meloxicam is about 7.5 mg. In another embodiment, the amount of meloxicam is about 15 mg. In a further embodiment, the weight percentage of meloxicam in the pharmaceutical composition is in the range of about 20% to 45%. In a further embodiment, the weight percentage of meloxicam is about 35% to 40%.

In some embodiments, the particle size of meloxicam may affect the bioavailability of meloxicam in the subject (e.g., $C_{max}$, the area under the plasma concentration-time curve (AUC), etc). In some embodiments, the particle size (D90) of meloxicam is in the range of about 5, 6, 7, 8, 9, or 10 to 30, 31, 32, 33, 34, 35, 36, 37, 38, 39, or 40 microns. In another embodiment, the particle size (D90) of meloxicam is in the range of about 15 to 30 microns. In one embodiment, the particle size (D90) of meloxicam is about 6 microns. In another embodiment, the particle size (D90) of meloxicam is about 18 microns. In one embodiment, the particle (D90) of meloxicam is about 21 microns. In a further embodiment, the particle size (D90) of meloxicam is about 26 microns.

In one embodiment, the pharmaceutical compositions described herein include, in addition to the meloxicam, a matrix network. The matrix network is formed by at least one matrix former. In some embodiments, the pharmaceutical composition is in a solid oral dosage form.

Exemplary matrix formers include, but are not limited to, materials derived from animal or vegetable proteins, such as gelatins, dextrins, soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

More exemplary matrix formers include, but are not limited to, sugars such as mannitol, dextrose, lactose, galactose and trehalose; cyclic sugars such as cyclodextrin; inorganic salts such as sodium phosphate, sodium chloride and aluminum silicates; and amino acids having from 2 to 12 carbon atoms such as a glycine, L-alanine, L-aspartic acid, L-glutamic acid, L-hydroxyproline, L-isoleucine, L-leucine and L-phenylalanine.

In some embodiments, the matrix network comprises at least one matrix former selected from gelatin, hydrolyzed dextran, and alginate.

In another embodiment, the matrix former comprises, consists essentially of or consists of gelatin and mannitol. In some embodiments, the amount of gelatin is in the range of about 10, 15, 20, or 25% to 30, 35, 40, 45, or 50% by weight of the pharmaceutical composition. In another embodiment, the amount of gelatin is in the range of about 28% to 33% by the weight of the pharmaceutical composition. Further, in one embodiment, the amount of mannitol is in the range of about 10% to 30% by weight of the pharmaceutical composition. In some embodiments, the amount of mannitol is in the range of about 20% to 25% by weight of the pharmaceutical composition.

The investigators of the present invention have discovered that the amount of gelatin and/or mannitol contributes to both the disintegration time and the mechanical properties (e.g., hardness, friability, etc.) of the oral dosage form of the pharmaceutical composition. Generally, a higher amount of gelatin and/or mannitol in the mixture will provide desired mechanical properties (e.g., harder tablet and lower friability), but longer disintegration time. In addition, in the process of preparing the pharmaceutical composition, a higher amount of gelatin and mannitol also increases the bulk viscosity of the mixture and consequently prevents meloxicam from settling during the dosing step. Therefore, in some embodiments of the invention, the amounts of gelatin and mannitol are adjusted in light of their impact on disintegration time, mechanical properties and/or the process of preparing the pharmaceutical compositions.

In one embodiment, the matrix network is obtained by freeze drying a mixture of a therapeutically effective amount of meloxicam, a dispersing agent, and a matrix former to a solid state.

In some embodiments, the pharmaceutical compositions described herein may use fish gelatin as a matrix former. (See, e.g., U.S. Pat. Nos. 6,709,669 and 7,325,703).

In one embodiment, the pharmaceutical compositions described herein comprise a porous network of matrix material that disperses rapidly in water. The matrix material is made up from at least about 0.1% by weight of a matrix former selected from gelatin, pectin, soy fibre protein and mixtures thereof, and one or more amino acids (e.g. glycine) having from about 2 to 12 carbon atoms and optionally mannitol. (See, e.g., U.S. Pat. Nos. 5,558,880 and 5,648,093).

The pharmaceutical compositions described herein may also include other excipients. Exemplary excipients include, but are not limited to, preservatives, antioxidants, surfactants, viscosity enhancers, coloring agents, flavors, pH modifiers, sweeteners and taste-masking agents.

Exemplary coloring agents include, but are not limited to, red, black and yellow iron oxides and FD&C dyes such as FD&C Blue No. 2 and FD&C Red No. 40, which are available from Ellis & Everard.

Exemplary flavoring reagents include, but are not limited to, mint, raspberry, licorice, orange, lemon, grapefruit, caramel, vanilla, cherry and grape flavors and/or combinations thereof.

The pH modifier may be any applicable acid or base. Exemplary pH modifiers include, but are not limited to, citric acid, tartaric acid, phosphoric acid, hydrochloric acid, maleic acid and sodium hydroxide.

Exemplary sweeteners include, but are not limited to, aspartame, acesulfame K and thaumatin.

Exemplary taste-masking agents include, but are not limited to, sodium bicarbonate, ion-exchange resins, cyclodextrin inclusion compounds, adsorbates or microencapsulated actives.

In one embodiment, the pharmaceutical compositions described herein further comprise at least one excipient selected from a pH modifier, sweetener and flavor. In one embodiment, the pH modifier is citric acid. In another embodiment, the sweetener is aspartame. In one embodiment, the flavor is orange.

In some embodiments, a modified starch may be included as a matrix former in the pharmaceutical compositions described herein. An exemplary formulation is further described in U.S. Pat. No. 6,509,040.

In another embodiment, surfactants are incorporated in the pharmaceutical compositions described herein to reduce foaming in mixing and improve wetting and dispersion in the mouth. An exemplary formulation and process are further described in U.S. Pat. No. 5,827,541.

In one embodiment, the pharmaceutical compositions described herein may further include an acid (e.g. citric acid)

to reduce the disintegration time in the fast dispersing dosage form, for example, as described in U.S. Patent Application Publication No. 20040156894.

In some embodiments, the pharmaceutical compositions described herein may also be in a controlled release dosage form. An exemplary formulation and process include, but are not limited to, those described in U.S. Pat. Nos. 6,413,549, and 5,976,577.

In some embodiments, the present invention may also apply to other fast disintegrating formulations known to one skilled in the art. Exemplary formulations that may be used in the present invention, include, but are not limited to, the formulations for Prosolv® ODT, PanExcea™ ODT, Pharmaburst® 500, Advatab®, Durasolv®, Orasolv®. In one embodiment, the formulation comprises microcrystalline cellulose, mannitol, fructose, and crospovidone. Further formulations include those described in U.S. Pat. No. 6,083,531.

III. Process for Preparing the Pharmaceutical Composition

Another aspect of the invention provides a process for preparing an oral dosage form of the pharmaceutical composition of meloxicam comprising the steps of (1) preparing a mixture of a therapeutically effective amount of meloxicam, at least one matrix former, and a dispersing agent ("mixing"); (2) filling said mixture into one or more depressions in a tray ("dosing"); (3) freezing said mixture in said trays so as to form a solid state of the mixture ("freezing"); and (4) removing the dispersing agent so as to form a solid tablet of the pharmaceutical composition ("drying").

(1) Step 1 (Also Referred to as "Mixing" Step)

In some embodiments, for step (1), the matrix formers are gelatin and mannitol. The investigators of the present invention have discovered that, in step 2, the precipitation rate of the meloxicam in the mixture may be adjusted by controlling the amount of gelatin and/or mannitol in the mixture. During step 2 of dosing, the active ingredient (e.g., meloxicam) in the suspension should precipitate evenly such that the amount of active ingredient in each dosage is uniformly distributed. Therefore, the amount of gelatin and/or mannitol added in the mixing step can be controlled within a range to prevent or substantially eliminate settling out of the drug particles. In some embodiments, the amount of gelatin is in the range of about 2.5% to 4.5% by weight of the mixture. In one embodiment, the amount of gelatin is about 3% to 4% by weight. In another embodiment, the amount of gelatin is about 4% by weight of the mixture. Further, in one embodiment, the amount of mannitol is in the range of about 1.5% to 3.5% by weight of the mixture. In another embodiment, the amount of mannitol is in the range of about 1.9% to 3% by weight of the mixture.

One or more matrix formers may be optionally incorporated into the mixture prior to step 2. In addition to forming the matrix, the matrix former may be helpful to maintain the dispersion of meloxicam within the mixture because meloxicam is not very soluble in water, which may result in a suspension rather than a solution. In some embodiments, the meloxicam is incorporated into the mixture by mixing at a speed of 1000 to 3000 rpm for about 10-60 minutes while maintaining the temperature in a range of about 10° C. to 40° C. In some embodiments, the meloxicam is incorporated into the mixture by mixing at a speed of 1500 to 2500 rpm for about 20-40 minutes while maintaining the temperature in the range of about 20° C. to 30° C. In some embodiments, the meloxicam is incorporated into the mixture by homogenizing at a speed of about 2000 rpm for up to about 35 minutes while maintaining the temperature in the range of about 21° C. to 25° C.

The investigators of the present invention have discovered that when the particle size of meloxicam is too large, the meloxicam particles tend to settle out too fast during step 2. Therefore, in some embodiments of the invention, the particle size of the meloxicam is controlled. In some embodiments, the particle size (D90) of meloxicam is in the range of about 5, 6, 7, 8, 9, or 10 to 30, 31, 32, 33, 34, 35, 36, 37, 38, 39, or 40 microns. In another embodiment, the particle size (D90) of meloxicam is in the range of about 15 to 30 microns. In one embodiment, the particle (D90) of meloxicam is about 6 microns. In another embodiment, the particle size (D90) of meloxicam is about 18 microns. In one embodiment, the particle (D90) of meloxicam is about 6 microns. In one embodiment, the particle (D90) of meloxicam is about 21 microns. In a further embodiment, the particle size (D90) of meloxicam is about 26 microns.

In some embodiments, a pH lower than neutral (7) is used to reduce or prevent microbial growth (e.g. during dosing). In another embodiment, the pH of the mixture is maintained in the range of about 4 to 5. In one embodiment, the pH of the mixture is in the range of about 4.3 to 4.7. In one embodiment, the pH of the mixture is maintained about 4.5. In one embodiment, the pH of the mixture is controlled by adding a pH modifier. Further, in one embodiment, the pH modifier is citric acid.

In some embodiments, the dispersing agent is water.

(2) Step 2 (Also Referred to as "Dosing" Step)

The investigators of the present invention have discovered that the temperature during the dosing can be controlled to optimize the process. If the temperature is too high, the meloxicam tends to settle out of the mixture too fast and then the amount of meloxicam in each dosage is not distributed evenly. If the temperature is too low, the mixture from step 1 may form a gel such that the meloxicam does not settle out during the dosing step. In addition, a low temperature during the dosing step provides desirable mechanical properties to the pharmaceutical compositions described herein; however, it may prolong the disintegration time.

In one embodiment, the temperature for step (2) is in the range of about 5° C. to 40° C., or 15° C. to 30° C. In another embodiment, the temperature for step (2) is in the range of about 19° C. to 25° C. In another embodiment, the temperature for step (2) is in the range of about 19° C. to 23° C.

(3) Step 3 (Also Referred to as "Freezing" Step)

The temperature is selected for step (3) to ensure that the formulation is completely frozen. In some embodiments the temperature is in the range −50 to −100° C. or −70 to −90° C.

(4) Step 4 (Also Referred to as "Drying" Step)

In one embodiment, for step (4), the dispersing agent is removed by freeze drying. The pressure, temperature and time of the freeze drying is controlled to ensure all frozen water is removed resulting in a uniformly dried product with satisfactory appearance and mechanical strength.

In some embodiments, the drying step is maintained under a temperature in the range of about 0° C. to 5, 10, 15, 20, 25 or 30° C. for about 60 to 120, 180, 240, 320 or 360 minutes. In some embodiments, the drying step is maintained under a temperature in the range of about 0° C. to 5° C. for about 360 minutes. In some embodiments, the drying step is maintained at a temperature at least 0° C. for about 360 minutes.

In a further embodiment, the process for preparing the pharmaceutical formulation comprises a method of formulating a pharmaceutically active substance that has an unpalatable taste as described in U.S. Pat. Nos. 6,726,928, 5,837,287, and 5,738,875.

In another embodiment, xanthan gum is included in the process for preparing the pharmaceutical compositions described herein to enhance homogeneity of the suspension and dose-content uniformity of the drug. An exemplary process is further described in U.S. Pat. No. 5,631,023.

The pharmaceutical compositions described herein may be packaged by any appropriate method or in any applicable form known to one skilled in the art. An exemplary packaging process or procedure (e.g., blister pack optionally with indicia, embossed blister pack, multi-laminate pack) include, but are not limited to, those described in U.S. Pat. Nos. 6,212,791, 5,457,895, 5,729,958, 5,343,672, 6,890,472, 7,121,822 and U.S. Patent Application Publication No. 2005/0181182A1. Further exemplary packaging processes or procedures are described in U.S. Pat. Nos. 6,830,153, 5,046,618, 5,358,118 and 6,588,180.

General information regarding fast dissolving oral dosage forms and processes are also described in U.S. Pat. Nos. 4,305,502 and 4,371,516, GB Patent No. 1548022 and GB Patent Application Publication No. 2111423.

IV. Methods of Treating Arthritis and/or Pain

Another aspect of the invention provides methods of preventing or treating arthritis and/or pain. The methods comprise orally administering to a subject in need thereof a therapeutically effective amount of a pharmaceutical composition as described herein. In one embodiment, the arthritis is selected from rheumatoid arthritis, Ankylosing spondylitis and osteoarthritis. The present invention may be used to treat any type of pain. In one embodiment, the pain is acute pain. In other representative embodiments, the pain is chronic pain. Nonlimiting examples of pain that can be treated according to the present invention include: lower back pain (e.g., due to degenerative disc disease), nerve pain (e.g., neuropathic pain, for example, pain due to diabetic neuropathy or neuropathic cancer), pain associated with multiple sclerosis, menstrual pain, bone pain (e.g., due to bone cancer or trauma or injury to the bone), pain associated with Familial Adenomatous Polyposis (FAP), pain due to gastrointestinal disorders (e.g., Crohn's disease, irritable bowel syndrome, acid reflux, diverticulitis or colitis), surgical pain, herpetic pain, and pain due to inflammation, injury or trauma.

The subject can be any mammalian or avian subject (as described herein). In some embodiments of the invention, the subject has or is at risk for arthritis and/or pain. In some embodiments, the subject is human. In one embodiment, the subject is a dog or a cat. Optionally, the subject is "in need of" the methods of the present invention, e.g., because the subject has or is believed to be at a risk of developing pain and/or arthritis.

A further aspect of the invention provides the use of the pharmaceutical compositions described herein for the manufacture of a medicament for the treatment of arthritis or pain.

Further provided are the pharmaceutical compositions described herein for the treatment of arthritis or pain.

It is understood that the combination of all embodiments described herein is also envisaged in the present invention.

The present invention will now be described in more detail with reference to the following examples. However, these examples are given for the purpose of illustration and are not to be construed as limiting the scope of the invention.

EXAMPLES

I. Exemplary Process

An exemplary manufacturing process for the oral lyophilizate dosage form of meloxicam may include five stages; mixing, dosing, freezing, freeze-drying and packaging. These stages are described below and in FIG. 1.

1. Mixing

The gelatin, mannitol and purified water are dispersed and heated to dissolve the matrix components. In some situation, the mixture of purified water mannitol and gelatin may be heated to 60° C. for 60 mins to ensure that mannitol and gelatin are dissolved. Then, the mixture is cooled to the desired temperature (e.g., 23° C.) and filtered into a suitable vessel. Once the filtration is complete, the solution is returned to the mixing vessel. Aspartame and orange flavor are then added to the above mixture. A quantity of citric acid is then added for pH adjustment. Meloxicam is then added to the mixture. A final quantity of purified water is then added to ensure that the weight of the materials dispensed for the batch meets the required batch weight. Addition of the final quantity of purified water reflects the small variability in the amount of citric acid required for the pH adjustment.

2. Dosing

Positive displacement pumps (or any pump of equivalent performance) are used to dose accurate amounts of the suspension into preformed blister pockets.

3. Freezing

The drug suspension is frozen when trays containing multiple blister cards pass through a liquid-nitrogen freezing tunnel. The temperature of the tunnel and time the cards remain in the tunnel are controlled to ensure frozen units are manufactured. After freezing, the trays of frozen product are stored in freezers which are temperature controlled and monitored to ensure that the units remain frozen throughout the frozen storage period.

4. Freeze Drying

The trays of frozen product are then placed in a freeze-dryer and dried. The freeze-drying process removes the frozen water rapidly by sublimation at low pressure. Once dried, the product is transferred to dry storage cabinets and held in a temperature and humidity controlled environment while in-process inspection and tablet weight and dispersion tests are conducted. On successful completion of the in-process tests the dried product is transferred to the packaging line for application of the lidding foil.

5. Packaging

The packaging is a continuous process that starts at the first stages of the manufacturing process. The process is summarized as follows: a) blister pockets are formed in the blister-forming machine, b) blister pockets are filled with the product and cut into trays, c) blister trays are frozen on the filling line, d) blister trays are freeze-dried in the freeze-dryer, e) lidding foil is heat sealed to the blister film, f) the packs are perforated or cut as required, and g) the blister cards are bulk packed into shipping cartons for subsequent secondary packaging.

II. Exemplary Formulation

There are two different dosage forms of meloxicam. Each dosage form contains 7.5 mg or 15 mg of meloxicam respectively. Both dosage forms of meloxicam are orange flavored, yellow, circular tablets and debossed with a suitable image.

The composition of the dosage forms is shown in Table 1.

TABLE 1

| Name of Ingredient | Quantity per 7.5 mg tablet (mg) | Quantity per 15 mg tablet (mg) | Function | Reference to Standards |
|---|---|---|---|---|
| Active ingredient | | | | |
| Meloxicam | 7.5 | 15.0 | Active Ingredient | USP |
| Other | | | | |

TABLE 1-continued

| Name of Ingredient | Quantity per 7.5 mg tablet (mg) | Quantity per 15 mg tablet (mg) | Function | Reference to Standards |
|---|---|---|---|---|
| Ingredients: | | | | |
| Purified Water[1] | Qs to 150.00 mg | Qs to 300.00 mg | Dispersing agent | USP |
| Gelatin (DGF) | 6 | 12 | Matrix former | USP NF |
| Mannitol | 4.5 | 9 | Matrix former | USP |
| Citric Acid | Qs to pH 4.5 | Qs to pH 4.5 | pH modifier | USP |
| Aspartame | 0.53 | 1.05 | Sweetener | USP NF |
| Orange 501071AP 0551 | 0.75 | 1.5 | Flavour | In-House |
| Total wet dosing weight | 150.00 | 300.00 | | |
| Theoretical total dry tablet weight | 18.55-20.51 | 37.11-41.01 | | |

[1] Not present in the finished product. Only residual quantities present in the finished product after freeze drying.

Both dosage forms are packaged in aluminum blister packs. The blister pack comprises a multi-layered (e.g. 5 layers) laminated blister film and a lidding foil. The lidding foil is peelable such that the lidding foil over each tablet may be removed to reach the tablet.

III. Exemplary Equipment for Preparing the Dosage Form of Meloxicam

An exemplary apparatus for the manufacture of the oral lyophilizate dosage form of meloxicam is provided in Table 2 below along with the exemplary processing steps shown in Example I above and FIG. 1.

TABLE 2

| Process steps | | Equipment |
|---|---|---|
| Mixing | Pre-mix | Vacuum mixer or equivalent |
| Dosing | Suspension storage | Intermediate Storage Vessel (ISV) or equivalent |
| | Blister Forming | Form Filler |
| | Dosing Pumps | Positive Displacement Pumps |
| Freezing | | Liquid Nitrogen Freeze Tunnel |
| Frozen storage | | Refrigerated Storage Cabinets (RSC) |
| Freeze Drying | | Freeze Dryer |

TABLE 2-continued

| Process steps | Equipment |
|---|---|
| Dry Storage | Dry Storage Cabinet (DSC) |
| Packaging | Sealer |

IV. Bioavailability Study of Meloxicam Orally Disintegrating Tablets 15 mg

An open-label, balanced, randomized, three-treatment, three-period, six-sequence, single-dose, crossover relative bioavailability study of Meloxicam tablets 15 mg (Melox ODT 15 mg) versus Mobic® tablets (containing 15 mg meloxicam) in 17 normal healthy, adult, male, human subjects under fasting conditions was carried out. The Melox ODT 15 mg was manufactured by Catalent UK Swindon Zydis Limited, Swindon, UK SN5 8RU. The formulation of Melox ODT 15 mg is the same as those described in Example, part II, exemplary formulation. The Mobic® tablets was manufactured by Boehringer Ingelheim Mexico.

The particle size (D90) of meloxicam in Batch No. 1024674 (test product A) is about 18 microns. The particle size (D90) of meloxicam in Batch No. 1027296 (test product B) is about 6 microns. The products, dose and mode of administration, batch number are shown in Table 3:

TABLE 3

| Type of product | Name with strength | Batch No. | Particle Size (D90) | Dose and mode of administration |
|---|---|---|---|---|
| Test (A) | Melox ODT 15 mg | 1024674 | About 18 microns | In each study period, a single oral dose of test product (A) Melox ODT 15 mg was placed on the tongue and the subjects swallowed once the tablet has completely dissolved. Subjects were dosed in sitting posture as per the randomization schedule under fasting conditions. |
| Test (B) | Melox ODT 15 mg | 1027296 | About 6 microns | In each study period, a single oral dose of test product (B) Melox ODT 15 mg was placed on the tongue and the subjects swallowed once the tablet has completely dissolved. Subjects were dosed in sitting posture as per the randomization schedule under fasting conditions. |
| Reference (C) | Mobic ® (Meloxicam) tablets 15 mg | 951156 | | In each study period, a single oral dose reference tablet (C) Mobic ® tablet (containing 15 mg of meloxicam) was administered along with 240 ± 2 mL of room temperature water. Subjects were dosed in sitting posture as per the randomization schedule under fasting conditions. |

The pharmacokinetics of test product A and B and reference product C were evaluated by the estimation of relative bioavailability of meloxicam in plasma. The test was carried out by methods known to one skilled in the art. The pharmacokinetic parameters, peak plasma concentration ($C_{max}$), The area under the plasma concentration versus time curve from 0 to the last measurable concentration ($AUC_{0-t}$), and the area under the plasma concentration versus time curve from 0 to infinity ($AUC_{0-inf}$), were tested. The mean and standard deviation (SD) of pharmacokinetic parameters for test products A, B and reference product C for Meloxicam are shown in Table 4.

TABLE 4

| Parameters | Un-transformed Data (n = 17) Mean ± SD | | |
|---|---|---|---|
| (Units) | Test - A | Test - B | Reference - C |
| *$T_{max}$ (hr) | 4.00 | 4.00 | 4.50 |
| $C_{max}$ (ng/mL) | 2076.446 ± 586.0383 | 2553.297 ± 678.3123 | 2027.545 ± 672.4808 |
| $AUC_{0-t}$ (ng · hr/mL) | 40259.795 ± 7893.9161 | 42832.889 ± 8081.2545 | 38575.949 ± 8693.1468 |
| $AUC_{0-inf}$ (ng · hr/mL) | 69432.373 ± 18812.4577 | 70053.574 ± 19024.5855 | 68208.928 ± 23475.3064 |
| $\lambda_z$ (1/hr) | 0.028 ± 0.0070 | 0.029 ± 0.0066 | 0.028 ± 0.0075 |
| $t^{1/2}$ (hr) | 26.469 ± 6.4686 | 24.817 ± 5.7895 | 26.873 ± 7.9491 |

*Median values reported for $T_{max}$

The geometric least squares mean, ratio of Test Product-A, Test Product-B and Reference Product-C, (i.e. (A/C) %, (B/C) % and 90% confidence intervals for the ln-transformed pharmacokinetic parameters $C_{max}$, $AUC_{0-t}$, $AUC_{0-inf}$) for meloxicam are shown in Tables 5 and 6.

TABLE 5

| | Least Squares Means | | |
|---|---|---|---|
| Parameters (Units) | Test-A | Test-B | Reference-C |
| $C_{max}$ (ng/mL) | 2001.333 | 2465.894 | 1926.368 |
| $AUC_{0-t}$ (ng · hr/mL) | 39542.795 | 42157.962 | 37745.538 |
| $AUC_{0-inf}$ (ng · hr/mL) | 66775.63 | 67380.975 | 64352.047 |

TABLE 6

| Parameters | Ratio of Least Squares Means | | 90% Confidence Limits (%) | |
|---|---|---|---|---|
| (Units) | (A/C) % | (B/C) % | (A vs. C) | (B vs. C) |
| $C_{max}$ (ng/mL) | 103.9 | 128.0 | 95.92-112.53 | 118.19-138.65 |
| $AUC_{0-t}$ (ng · hr/mL) | 104.8 | 111.7 | 99.70-110.08 | 106.29-117.36 |
| $AUC_{0-inf}$ (ng · hr/mL) | 103.8 | 104.7 | 94.29-114.19 | 95.14-115.23 |

As demonstrated in Tables 4-6, the bioavailability for Test product A (D90=about 18 microns) is similar to the reference product-C (Mobic®). The bioavailability for Test product B (D90=about 6 microns) is improved compared to the reference product-C.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A pharmaceutical composition in a dosage form comprising a therapeutically effective amount of meloxicam, or a pharmaceutically acceptable salt thereof, wherein the pharmaceutical composition is in the form of a fast disintegrating dosage form suitable for releasing meloxicam rapidly in the oral cavity and the particle size (D90) of meloxicam is in the range of about 5 to 40 microns.

2. The composition of claim 1, wherein meloxicam is released in less than about 30 seconds in the oral cavity.

3. The composition of claim 1, wherein meloxicam is released in less than about 10 seconds in the oral cavity.

4. The composition of claim 1, wherein meloxicam is released in less than about 3 seconds in the oral cavity.

5. The composition of claim 1, wherein meloxicam is selected from the group consisting of crystalline phase, an amorphous phase, a semi-crystalline phase, a semi-amorphous phase, and a combination thereof.

6. The composition of claim 1, wherein the amount of meloxicam is added in the range of about 5 mg to 20 mg.

7. The composition of claim 1, wherein the amount of meloxicam is in the range of about 20% to 45% by weight of the pharmaceutical composition.

8. The composition of claim 1, further comprising a matrix network.

9. The composition of claim 8, wherein the matrix network comprises at least one matrix former selected from gelatin, hydrolyzed dextran, and alginate.

10. The composition of claim 8, wherein the matrix former is a combination of gelatin and mannitol.

11. The composition of claim 10, wherein the amount of gelatin is in the range of about 15% to 40% by weight of the pharmaceutical composition.

12. The composition of claim 10, wherein the amount of gelatin is in the range of about 28% to 33% by weight of the pharmaceutical composition.

13. The composition of claim 10, wherein the amount of mannitol is in the range of about 10% to 30% by weight of the pharmaceutical composition.

14. The composition of claim 10, wherein the amount of mannitol is in the range of about 20% to 25% by weight of the pharmaceutical composition.

15. The composition of claim 8, wherein the matrix network is obtained by freeze drying a mixture of a therapeutically effective amount of meloxicam, a dispersing agent, and a matrix former to a solid state.

16. The composition of claim 8, further comprising at least one excipient selected from a pH modifier, sweetener and flavor.

17. The composition of claim 16, wherein the pH modifier is citric acid.

18. The composition of claim 16, wherein the sweetener is aspartame.

19. The composition of claim 16, further comprising a taste masking agent and/or a coloring agent.

20. The composition of claim 1 packaged in a blister pocket.

21. The composition of claim 1, wherein the particle size (D90) of meloxicam is in the range of about 15 to 30 microns.

22. The composition of claim 1, wherein the particle size (D90) of meloxicam is in the range of about 18 to 21 microns.

23. The composition of claim 1, wherein the particle size (D90) of meloxicam is in the range of about 5 to 10 microns.

24. The composition of claim 1, wherein the particle size (D90) of meloxicam is about 6 microns.

* * * * *